(12) United States Patent
Hiraoka

(10) Patent No.: US 8,197,396 B2
(45) Date of Patent: Jun. 12, 2012

(54) TREATMENT TOOL FOR ENDOSCOPE AND MEDICAL PROCEDURE

(75) Inventor: Jin Hiraoka, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1368 days.

(21) Appl. No.: 11/411,276

(22) Filed: Apr. 26, 2006

(65) Prior Publication Data

US 2007/0255311 A1    Nov. 1, 2007

(51) Int. Cl.
 *A61B 1/00* (2006.01)
 *A61B 17/00* (2006.01)
(52) U.S. Cl. ................... 600/104; 600/106; 606/206
(58) Field of Classification Search .............. 600/104, 600/106, 154, 107, 153; 606/205–209
See application file for complete search history.

(56) References Cited

U.S. PATENT DOCUMENTS

| | | | | |
|---|---|---|---|---|
| 4,763,670 | A * | 8/1988 | Manzo | 600/569 |
| 5,312,432 | A * | 5/1994 | Pingleton et al. | 606/205 |
| 6,520,954 | B2 * | 2/2003 | Ouchi | 606/1 |
| 7,727,144 | B2 | 6/2010 | Suzuki | |
| 2005/0049455 | A1 * | 3/2005 | Ootawara et al. | 600/107 |
| 2007/0276180 | A1 * | 11/2007 | Greenburg et al. | 600/106 |

FOREIGN PATENT DOCUMENTS

| | | |
|---|---|---|
| EP | 0 260 466 | 3/1988 |
| EP | 1 518 492 A1 | 3/2005 |
| EP | 1 554 974 A1 | 7/2005 |
| JP | S62-253041 | 11/1987 |
| JP | H05-237120 | 9/1993 |
| JP | 2000-201939 | 7/2000 |
| JP | 2000-342516 | 12/2000 |
| JP | 2005-137816 | 6/2005 |
| JP | 2005-198868 | 7/2005 |
| JP | 2005-312828 | 11/2005 |

OTHER PUBLICATIONS

Japanese Office Action dated Jul. 6, 2010 with English translation.

* cited by examiner

*Primary Examiner* — Anhtuan Nguyen
*Assistant Examiner* — Ryan Henderson
(74) *Attorney, Agent, or Firm* — Scully, Scott, Murphy & Presser, PC

(57) ABSTRACT

A treatment tool for an endoscope according to the present invention includes: an outer sheath to be inserted into a channel of an endoscope; a forcep sheath which is movably arranged in the outer sheath along an axial direction; a plurality of forcep cups which are attached to a distal end of the forcep sheath, at least one of which is formed with a sharp needle-shaped portion on a distal end, and which cooperate with each other to be openable/closable as a whole; an operation wire which is movably arranged in the forcep sheath along an axial direction, and is connected to the forcep cups, and which opens/closes the forcep cups when moved in its axial direction; a first operation portion which is movably attached along an axial direction of a proximal end of the outer sheath, and is connected to a proximal end of the forcep sheath; and a second operation portion which is movably attached to the first operation portion along an axial direction of the proximal end of the forcep sheath, and is connected to a proximal end of the operation wire.

10 Claims, 23 Drawing Sheets

TREATMENT TOOL FOR ENDOSCOPE AND MEDICAL PROCEDURE

BACKGROUND OF THE INVENTION

1. Field of the Invention

The present invention relates to a treatment tool for an endoscope and a medical procedure using this.

2. Description of Related Art

Recently, there is a demand for biopsy of the inside of a human parenchymatous organ and diagnosis of the tissue under an endoscope.

To meet such a demand, there is disclosed in Japanese Unexamined Patent Application, First Publication No. H05-237120 and Japanese Unexamined Patent Application, First Publication No. 2000-201939, a treatment tool for an endoscope which is used by being inserted into a channel of an endoscope, and has distal ends of a pair of openable/closable forcep cups formed into sharp needle-shapes.

In such a treatment tool for an endoscope, while being set into the channel of the endoscope, the pair of forcep cups are piercingly poked to the diagnosis site inside the parenchymatous organ using the sharp needle-shaped portion on the distal ends, and the forcep cups are further pushed forward while being opened so that the forcep cups reach the diagnosis site. Then, by closing the forcep cups, the biopsy tissue of the diagnosis site is collected.

SUMMARY OF THE INVENTION

An object of the present invention is to provide a treatment tool for an endoscope and a medical procedure which enable even only one operator to extremely readily perform two operations of opening forcep cups and pushing the forcep cups forward, which have to be performed at the same time, for collecting a biopsy tissue inside the parenchymatous organ.

The treatment tool for an endoscope according to the present invention includes: an outer sheath to be inserted into a channel of an endoscope; a forcep sheath which is movably arranged in the outer sheath along an axial direction; a plurality of forcep cups which are attached to a distal end of the forcep sheath, at least one of which is formed with a sharp needle-shaped portion on a distal end, and which cooperate with each other to be openable/closable as a whole; an operation wire which is movably arranged in the forcep sheath along an axial direction, and is connected to the forcep cups, and which opens/closes the forcep cups when moved in its axial direction; a first operation portion which is movably attached along an axial direction of a proximal end of the outer sheath, and is connected to a proximal end of the forcep sheath; and a second operation portion which is movably attached to the first operation portion along an axial direction of the proximal end of the forcep sheath, and is connected to a proximal end of the operation wire.

The medical procedure according to an aspect of the present invention includes: a step of inserting and setting a forcep mainbody including: an outer sheath to be inserted into a channel of an endoscope; a forcep sheath which is movably arranged in the outer sheath along an axial direction; a plurality of forcep cups which are openably/closably attached to a distal end of the forcep sheath, and at least one of which is formed with a sharp tapered portion on a distal end; and a forcep wire which is movably arranged in the forcep sheath along an axial direction, and is connected to the forcep cups, and which opens/closes the forcep cups when moved in the axial direction, into the channel of the endoscope; a step of inserting the insertion portion of the endoscope having the forcep mainbody inserted and set into the channel, into a body cavity of an examinee; a step of moving the first operation portion connected to the proximal side of the forcep sheath, to a distal side along an axial direction of a proximal side of the outer sheath, and piercing a parenchymatous organ of an examinee with the distal end of the forcep cups; a step of moving the first operation portion to the distal side along the axial direction of the proximal side of the outer sheath, moving the second operation portion that is movably attached to the first operation portion along an axial direction of a proximal end of the forcep sheath, and is connected to the proximal end of the operation wire, to the distal side along the axial direction of the proximal side of the outer sheath, and thereby moving the plurality of forcep cups forward while opening them; and a step of moving the second operation portion to the proximal side along the axial direction of the proximal side of the outer sheath, so as to close the forcep cups, and thereby correcting a biopsy tissue from the parenchymatous organ of the examinee.

DESCRIPTION OF THE PREFERRED EMBODIMENT

Hereunder is a detailed description of an embodiment.

Note that in the modified examples explained later, the same reference symbols are used for the same components, and duplicate descriptions are omitted.

Figure 1:
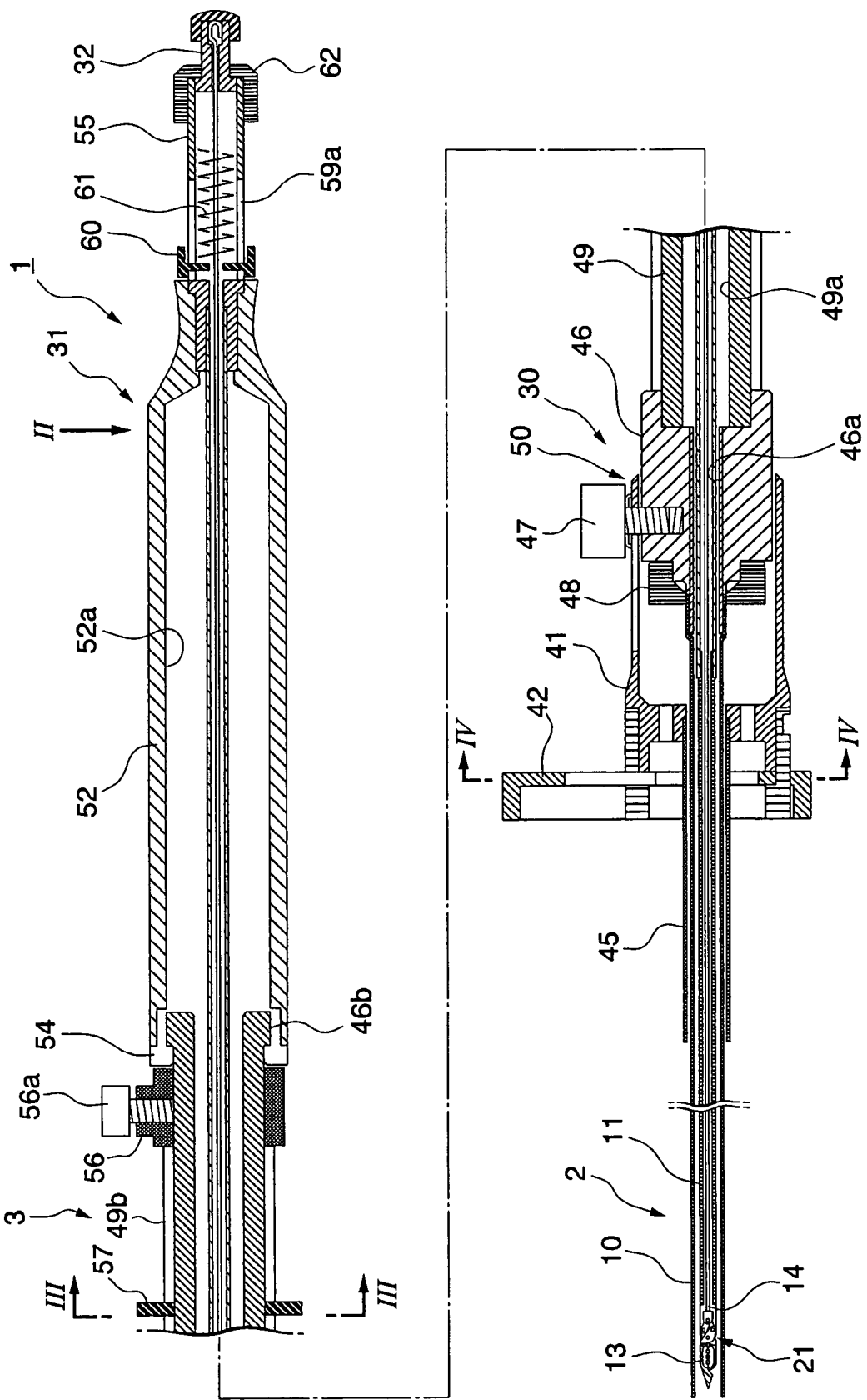
FIG. 1 is a cross-sectional view showing the whole of a treatment tool for an endoscope according to an embodiment.
Figure 2:
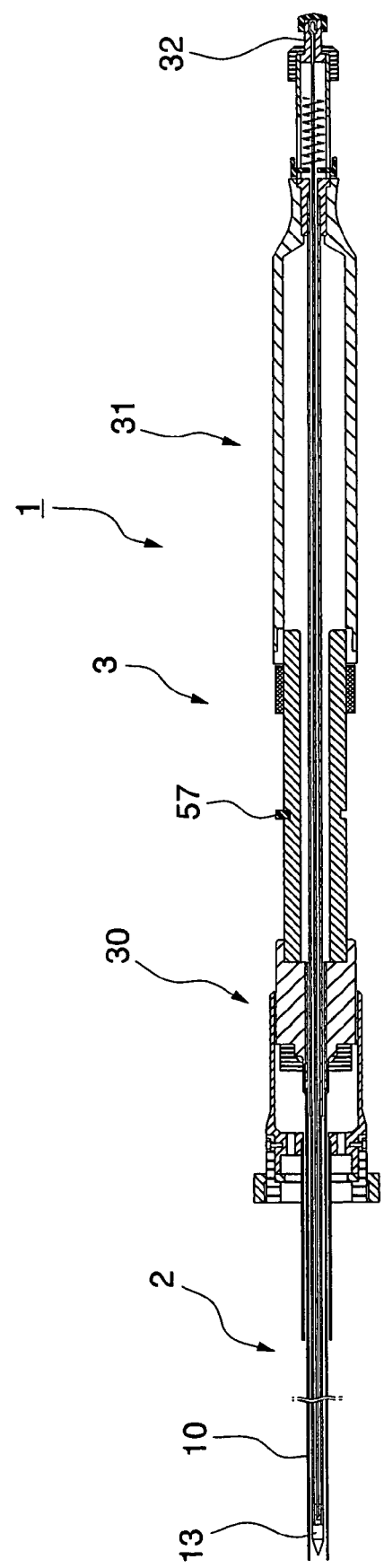
FIG. 2 is a cross-sectional view as viewed along the arrow II of FIG. 1.

FIG. 1 shows the whole of a treatment tool for an endoscope that is used by being inserted into a channel of an endoscope. The treatment tool for an endoscope 1 comprises: a forcep mainbody 2 for performing an actual treatment by being inserted into the channel of the endoscope; and an operation portion mainbody 3 for performing the positional adjustment of the forcep mainbody 2 with respect to the channel, and an opening/closing operation of the forcep cups.

The forcep mainbody 2 includes: an outer sheath 10 that is inserted into the channel of the endoscope; a coil sheath (forcep sheath) 11 movably arranged along the axial direction of the outer sheath 10 inside the outer sheath 10; a pair of forcep cups 13 attached to the distal end of the coil sheath 11 in a mutually openable/closable manner; and an operation wire 14 movably arranged along the axial direction of the coil sheath 11 inside the coil sheath 11, and connected to the forcep cups 13 so as to open/close the forcep cups 13 when the wire itself is moved in the axial direction.

In this specification, assuming that the treatment tool for an endoscope is inserted into the channel of the endoscope, then for the respective components of the treatment tool for an endoscope, the left side in FIG. 1 is referred to as the distal side and the right side is referred to as the proximal side.

The outer sheath 10 is made from a flexible pipe material, for example a tube of polytetrafluoroethylene or the like, so as to be deformable to follow the curvature of the insertion portion of the endoscope.

The coil sheath 11 is flexible, and for example, a closely coiled stainless steel wire is used, so that the pushing force from the proximal side can be transferred to the distal end.

Figure 5:
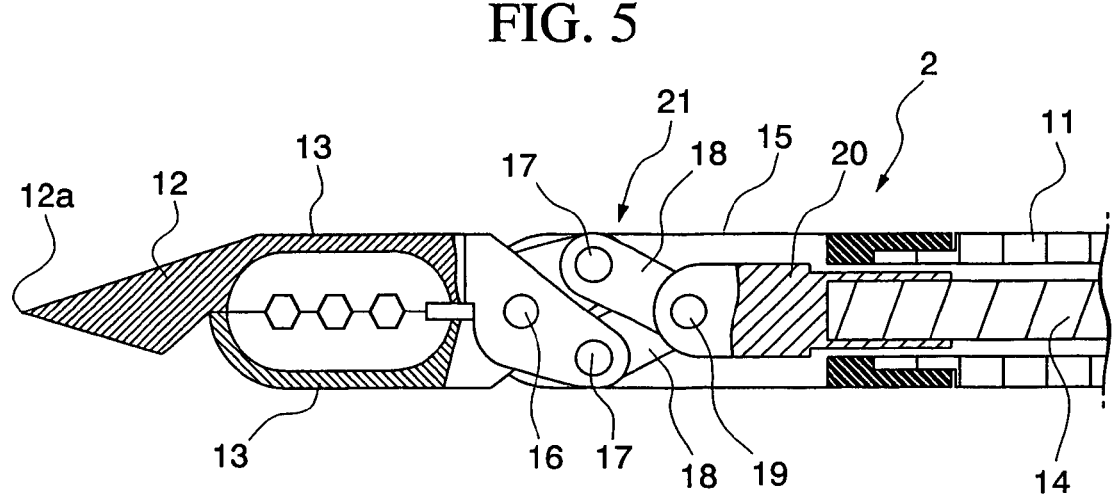
FIG. 5 is an enlarged side view for explaining the forcep cups of the treatment tool for an endoscope according to the embodiment.

As shown in FIG. 5, the pair of forcep cups 13 are formed into a cup-shape having a semicircular cross-section from the center to the distal end. The distal end of one forcep cup 13 of the pair of forcep cups 13 (here the top forcep cup in FIG. 5) is formed with a needle-shaped portion 12 which is sharp in a conical shape. The needle-shaped portion 12 is formed to project from one forcep cup to the other forcep cup side so as to project from the forcep cup main body to the distal side but within a range not interfering with the opening/closing operation of the forcep cups. Moreover, the distal center 12a of the needle-shaped portion 12 is arranged on the abutted portion positioned in the center of the pair of forcep cups 13.

The intermediate portions of the forcep cups 13 are rotatably attached via a pin 16 to a base plate 15 that is attached to the distal end of the coil sheath 11. Moreover, the proximal ends of the forcep cups 13 are respectively linked to the distal ends of link members 18 in a pair via pins 17. The proximal ends of the link members 18 are linked to a coupling rod 20 via a pin 19. The coupling rod 20 is linked to the distal end of the operation wire 14.

Figure 16:
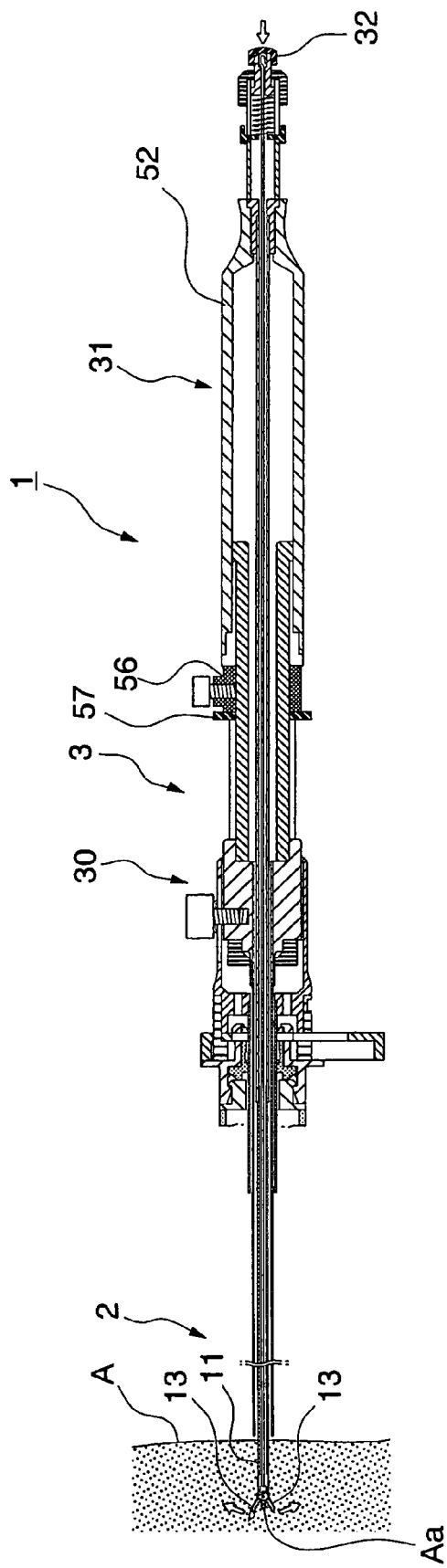
FIG. 16 is a cross-sectional view for explaining a step of the medical procedure according to the embodiment.
Figure 17:
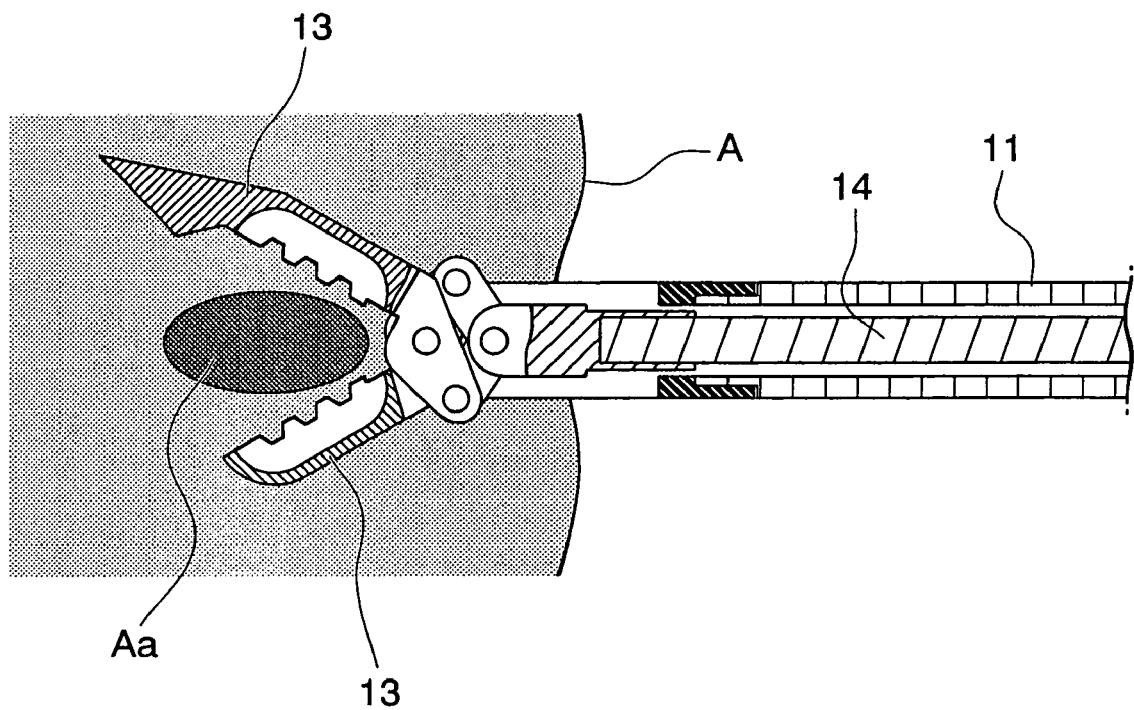
FIG. 17 is an enlarged cross-sectional view of the distal end of the treatment tool for an endoscope for explaining a step of the medical procedure according to the embodiment.
Figure 18:
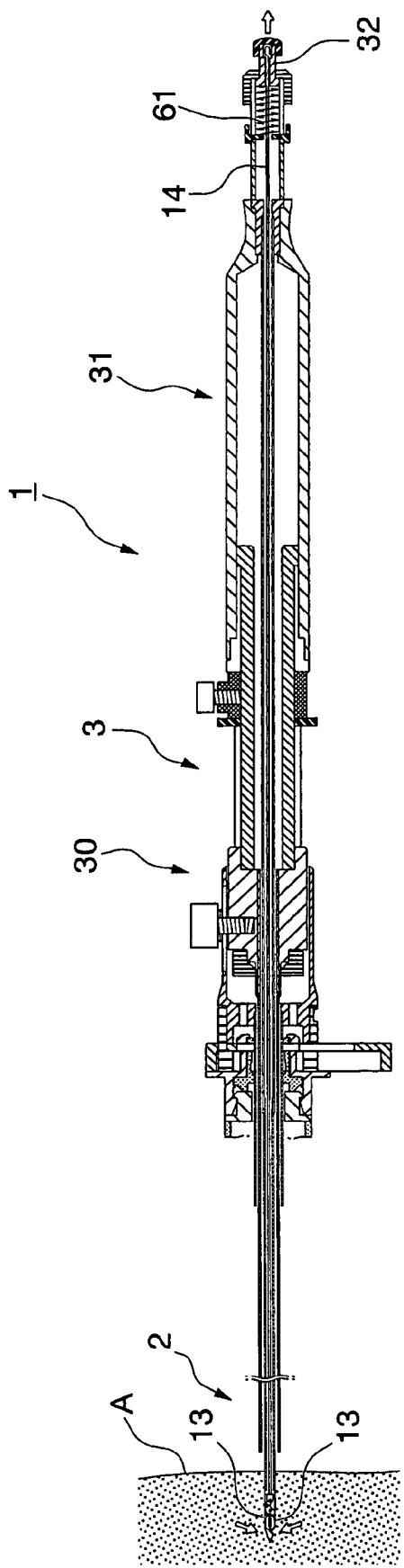
FIG. 18 is a cross-sectional view for explaining a step of the medical procedure according to the embodiment.

Moreover, the forcep cups 13, the link members 18, and the coupling rod 20 constitute a link mechanism 21. By this link mechanism 21, the pair of forcep cups 13 are opened when the operation wire 14 is moved to the distal side with respect to the coil sheath 11 as shown in FIG. 16 and FIG. 17, and the pair of forcep cups 13 are closed when the operation wire 14 is moved to the proximal side with respect to the coil sheath 11 as shown in FIG. 18.

The operation portion mainbody 3 has main components of: an endoscope coupling tool 30 which is fixed to an insertion port of the channel of the endoscope, and is connected to the proximal end of the outer sheath 10; a slider (first operation portion) 31 which is movably attached to the endoscope coupling tool 30 along the axial direction of the proximal end of the outer sheath 10, and is connected to the proximal end of the coil sheath 11; and a button (second operation portion) 32 which is movably attached to this slider 31 along the axial direction of the proximal end of the coil sheath 11, and is connected to the proximal end of the operation wire 14.

Figure 4:
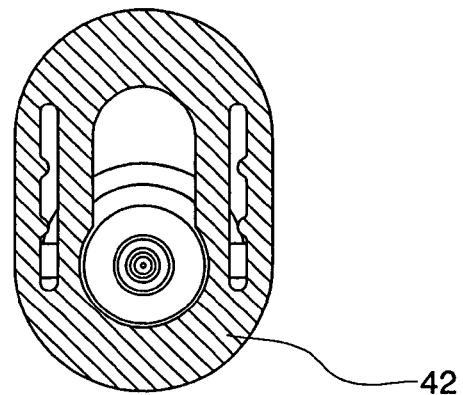
FIG. 4 is a cross-sectional view taken along the line IV-IV of FIG. 1.
Figure 8:
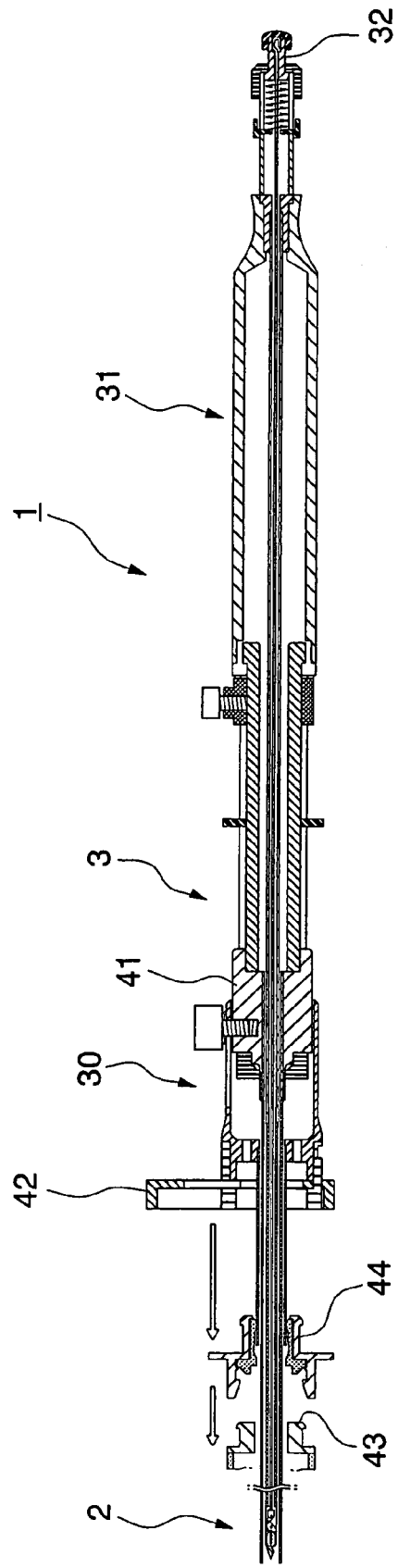
FIG. 8 is a cross-sectional view for explaining a step of the medical procedure according to the embodiment.

The endoscope coupling tool 30 is described here. Reference symbol 41 denotes a cylindrical coupling member installed coaxially with the insertion port 43 of the channel of the endoscope (refer to FIG. 8). As shown in FIG. 4, the distal end of this coupling member 41 is provided and arranged with a lock member 42 in a slidable manner in a direction orthogonal to the axis of the coupling member. As shown in FIG. 8, the coupling member 41 is fixed to the channel insertion port 43 of the endoscope via an adaptor forceps plug 44 in a fluid-tight condition, by sliding the lock member 42 downward in FIG. 10 while the adaptor forceps plug 44 to be fitted to the channel insertion port 43 of the endoscope is fitted inside.

The coupling member 41 is attached with an operation portion supporting pipe member 45 along the axis. This operation portion supporting pipe member 45 is fitted to the outside of the outer sheath 10.

Into the proximal side of the coupling member 41, the distal end of a pipe fixing member 46 is movably inserted along the axis of the coupling member 41. The fixed position of the pipe fixing member 46 with respect to the coupling member 41 can be optionally set by tightening a screw 47 with the coupling member 41 interposed therebetween.

The distal end of the pipe fixing member 46 is connected with the proximal end of the outer sheath 10 via a sheath fixing member 48. The proximal side of the pipe fixing member 46 is linked with a slider receiver 49 coaxially with the pipe fixing member 46. The coil sheath 11 is inserted respectively into through holes 49a and 46a formed along the axes of the slider receiver 49 and the pipe fixing member 46.

Here, the coupling member 41, the pipe fixing member 46, the slider receiver 49, and the like constitute the endoscope coupling tool 30. Moreover, the pipe fixing member 46, the screw 47, and the sheath fixing member 48 constitute a sheath fixed position adjustment mechanism 50 which adjusts the fixed position of the proximal end of the outer sheath 10 with respect to the coupling member 41.

Around the outer circumference on the proximal side of the slider receiver 49, the slider 31 is fitted to the outside of a slide groove 49b that is formed on the outer circumference of the slider receiver 49, and thereby the slider 31 is attached coaxially and movably in the axial direction with respect to the slider receiver 49. The slider 31 comprises: a slider mainbody 52 which is fitted to the outside of the slider receiver 49; a retaining member 54 attached to the distal side of the slider mainbody 52; and a coil sheath coupling member 55 attached to the proximal side of the slider mainbody 52.

Figure 15:
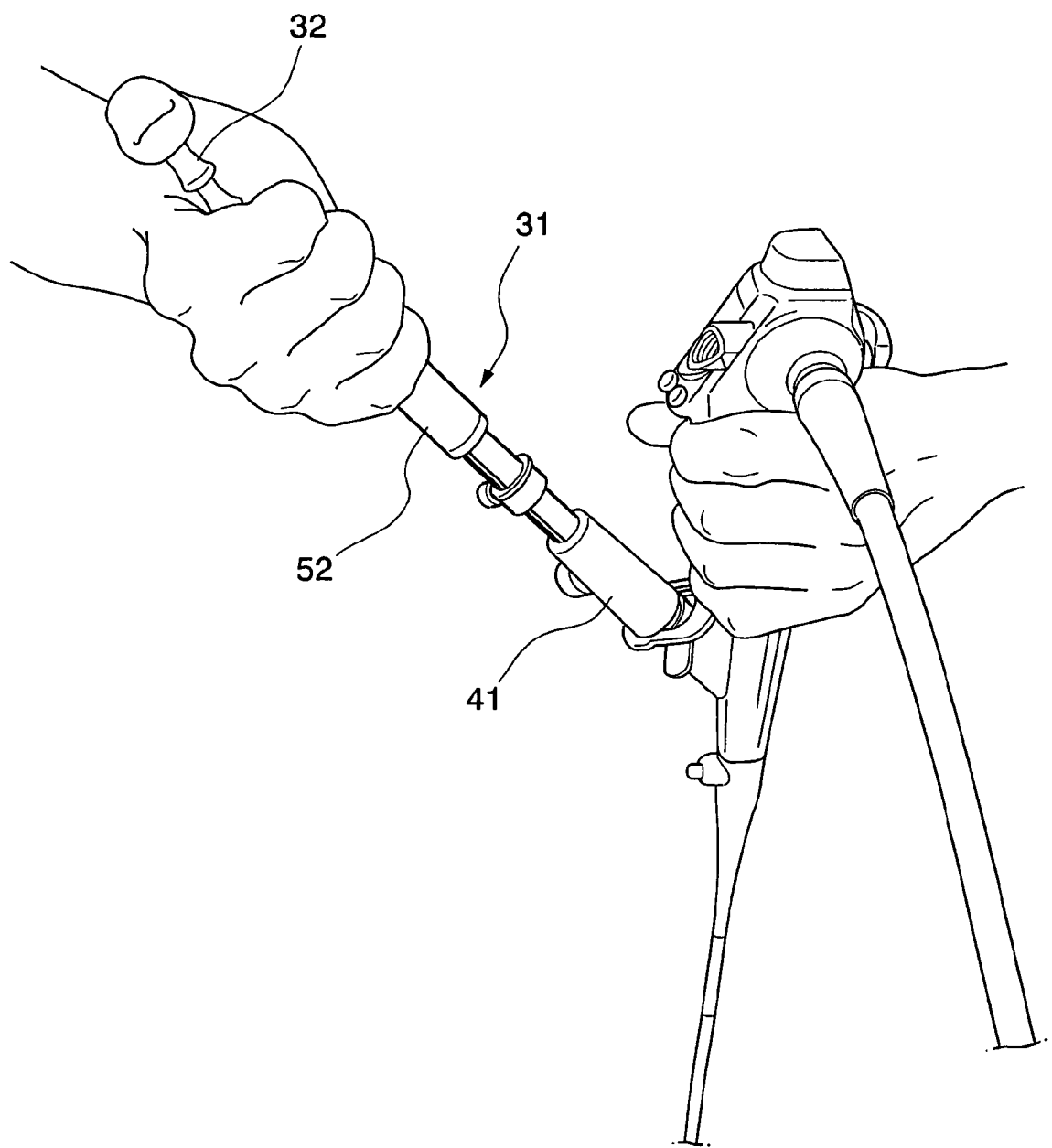
FIG. 15 is a perspective view of an operational situation using an operation portion mainbody for explaining a step of the medical procedure according to the embodiment.

The slider mainbody 52 is formed with a through hole 52a along the axis. Into this through hole 52a, the coil sheath 11 is inserted. As shown in FIG. 15, here, the slider mainbody 52 is constituted by a pipe-shaped handle that can be grasped by an operator with one hand.

The movement limit position of the slider mainbody 52 to the distal side with respect to the slider receiver 49 is determined by a stopper (first operation portion stopper) 56 that is movable in the axial direction and is fixed to the outer circumference of the slider receiver 49 in an optional position by means of a screw 56a. Moreover, the movement limit position of the slider mainbody 52 on the proximal side with respect to the slider receiver 49 is determined by the retaining member 54 abutted against an outer flange 46b formed on the proximal end of the slider receiver 49.

Here, when the slider mainbody 52 is moved to the distal side, the coil sheath coupling member 55, the coil sheath 11, and the forcep cups 13 are integrally moved in the same direction. Moreover, conversely, when the slider mainbody 52 is moved to the proximal side, the coil sheath coupling member 55, the coil sheath 11, and the forcep cups 13 are integrally moved in the same direction.

Figure 3:
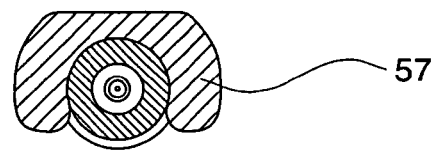
FIG. 3 is a cross-sectional view taken along the line III-III of FIG. 1.

The outer circumference of the approximate central portion of the slider receiver 49 is formed with a ring-like groove. As shown in FIG. 3, by means of a C ring 57 attached to this ring groove, the stopper 56 is restricted from being moved further to the distal side.

Figure 6:
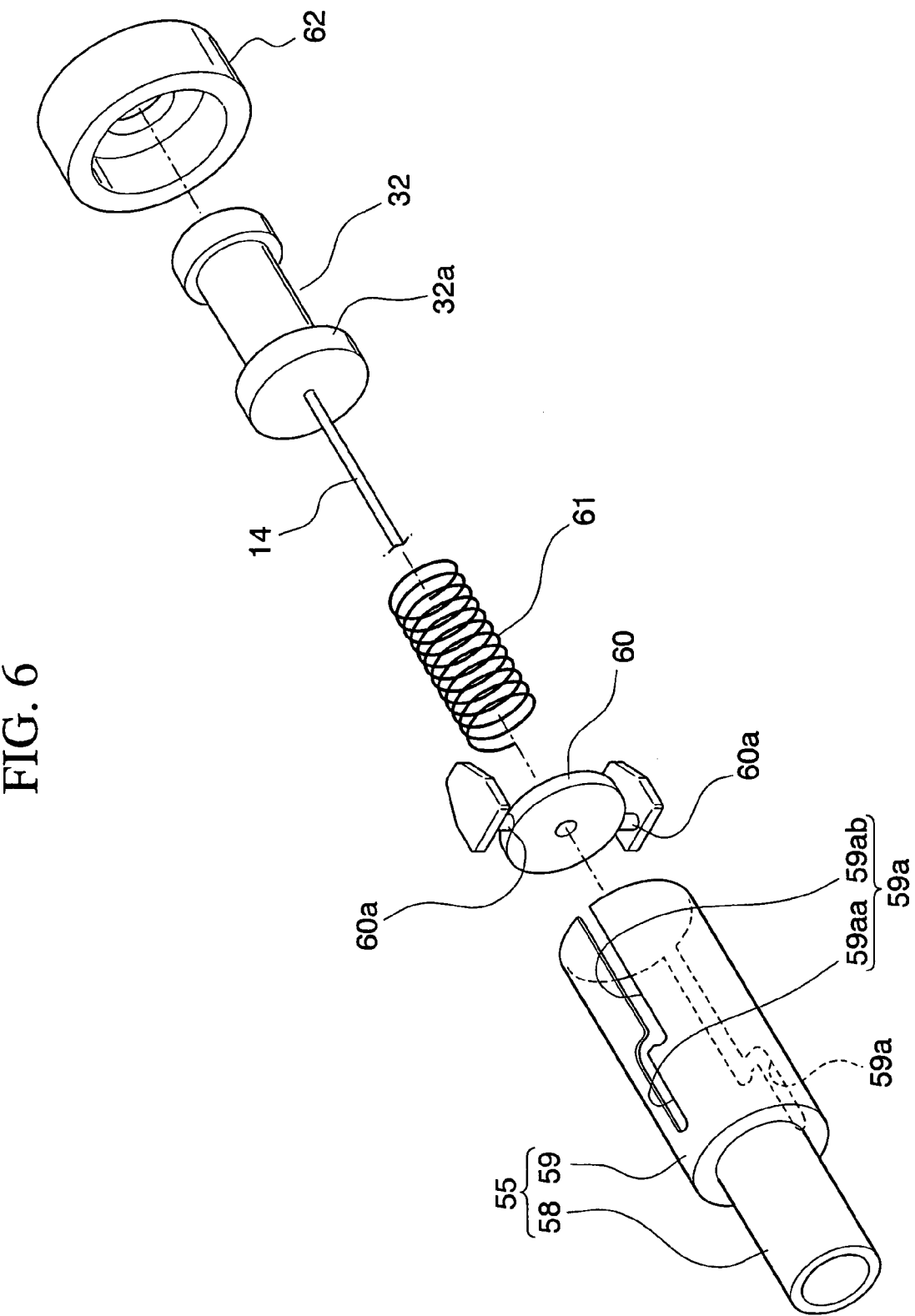
FIG. 6 is an enlarged exploded view of the proximal end of a slider mainbody of the treatment tool for an endoscope according to the embodiment.

As shown in FIG. 6, the coil sheath coupling member 55 is formed in a cylindrical shape overall, having a small diameter portion 58 on the distal side and a large diameter portion 59 on the proximal side. The small diameter portion 58 is inserted into the through hole formed in the proximal end of the slider mainbody 52, and fixed thereto. Moreover, with the proximal end of the coil sheath 11 inserted into the small diameter portion 58, this is fixed by an appropriate fixing means such as an adhesive.

Inside of the large diameter portion 59 of the coil sheath coupling member, from the distal side to the proximal side, a spring receiver (elastic member stopper) 60, a coil spring (elastic member) 61, and a part of the button 32 are stored. Moreover, the operation wire 14 is inserted into the large diameter portion 59 of the coil sheath coupling member, and the proximal end of the operation wire 14 is fixed to the button 32 as mentioned above.

The side wall of the large diameter portion 59 of the coil sheath coupling member 55 is formed with crank shape grooves 59a shifted through 180 degrees so as to be symmetrical to each other. In these crank shape grooves 59a are fitted neck portions 60a of the spring receiver 60. Moreover, depending on whether the neck portions 60a of the spring receiver 60 are latched on the longitudinal grooves 59aa of the crank shape grooves 59a or on the transverse grooves 59ab thereof, it can be alternatively selected whether the spring receiver 60 is in a position where it is always abutted against the coil spring 61, or is in a free position where it is not always abutted against the coil spring 61. That is, together with the neck portions 60a of the spring receiver 60, the crank shape grooves 59a of the large diameter portion 59 constitute a positioning mechanism which determines the position of the spring receiver 60.

Figure 7:
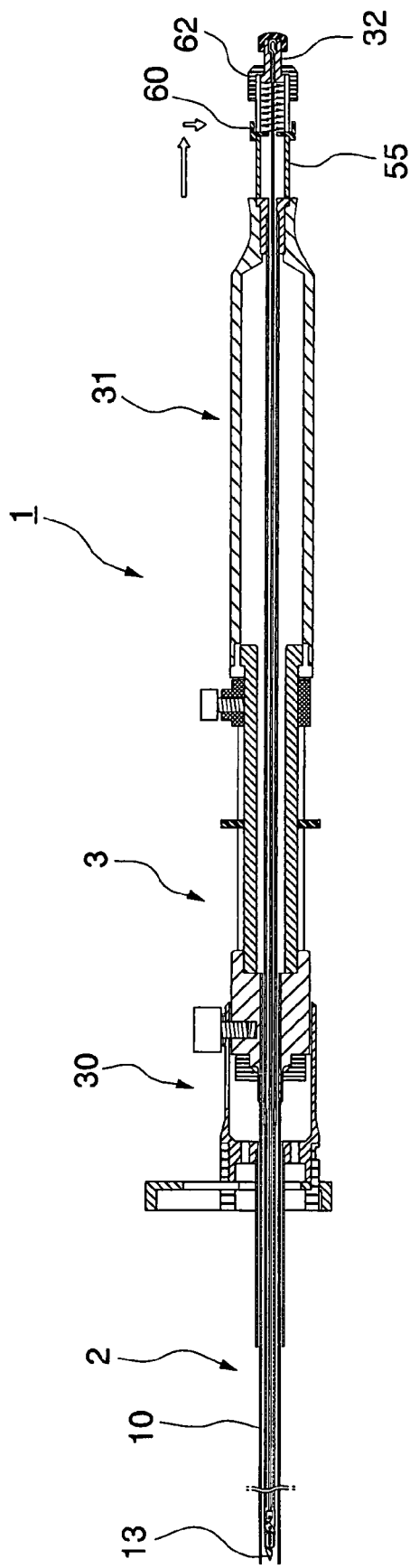
FIG. 7 is a cross-sectional view for explaining a step of a medical procedure according to the embodiment.

Moreover, when the spring receiver 60 is latched on the transverse grooves 59ab of the crank shape grooves 59, to be in a position where it is always abutted against the coil spring 61, that is in a condition shown in FIG. 7, then the button 32 is always pressed to the proximal side by the coil spring 61. In this condition, if the operator presses the button 32 to the distal side, the operation wire 14 is pushed to the distal side so as to open the forcep cups 13, and if the pressing on the button 32 is released, the operation wire 14 is pushed back to the proximal side due to the urging force of the coil spring 61, so as to close the forcep cups 13.

Onto the proximal end of the large diameter portion 59 of the coil sheath coupling member is fitted a cap 62. By latching this cap 62 on a large diameter portion 32a provided on the distal side of the button 32, the button 32 is prevented from dropping off.

Next is a description of a method of collecting a tissue of a parenchymatous organ of an examinee, using the treatment tool for an endoscope.

The previously sterilized treatment tool for an endoscope is taken out from a sterilized package. As shown in FIG. 7, the latched position of the neck portions 60a of the spring receiver 60 with respect to the crank shape grooves 59a of the large diameter portion is shifted from the longitudinal grooves 59aa to the transverse grooves 59ab, so as to set the spring receiver 60 to the position where it is always abutted against the coil spring 61. As a result, the coil spring 61 always urges the button 32 to the proximal side (right side in FIG. 7).

At the time of sterilization, the spring receiver 60 is in a position where its neck portions 60a are latched in the longitudinal grooves 59aa, in a free state where it is not always abutted against the coil spring 61. Therefore, the parts can be prevented from being abutted against each other, and the sterilization can be smoothly performed.

As described above, the treatment tool for an endoscope 1 having the spring receiver 60 set in the position where it is always abutted against the coil spring 61, is inserted from the insertion port 43 into the channel of the endoscope.

Figure 9:
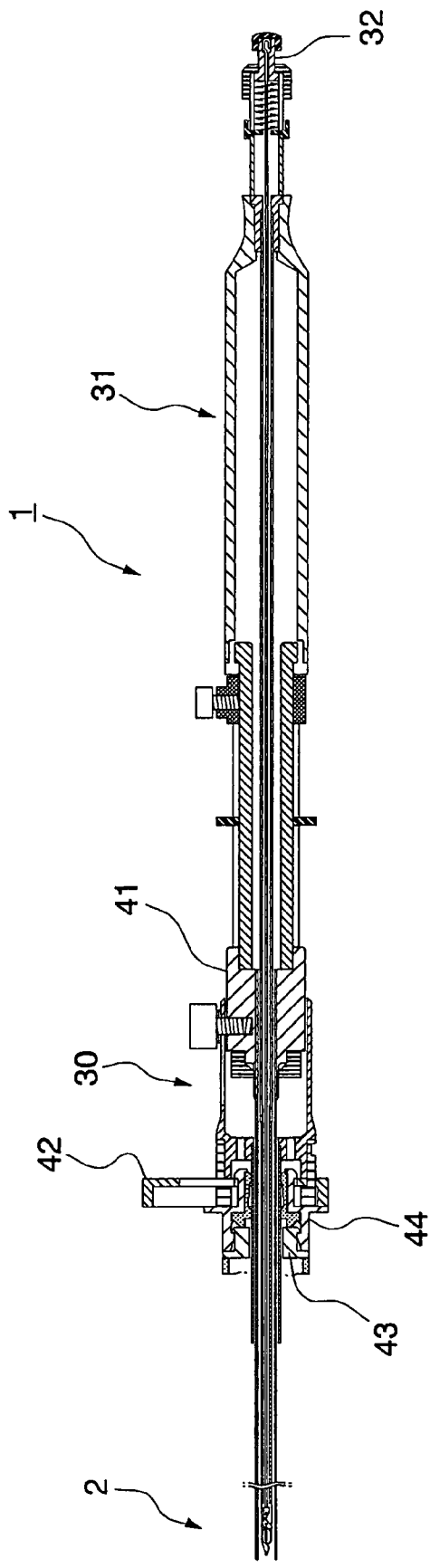
FIG. 9 is a cross-sectional view for explaining a step of the medical procedure according to the embodiment.
Figure 10:
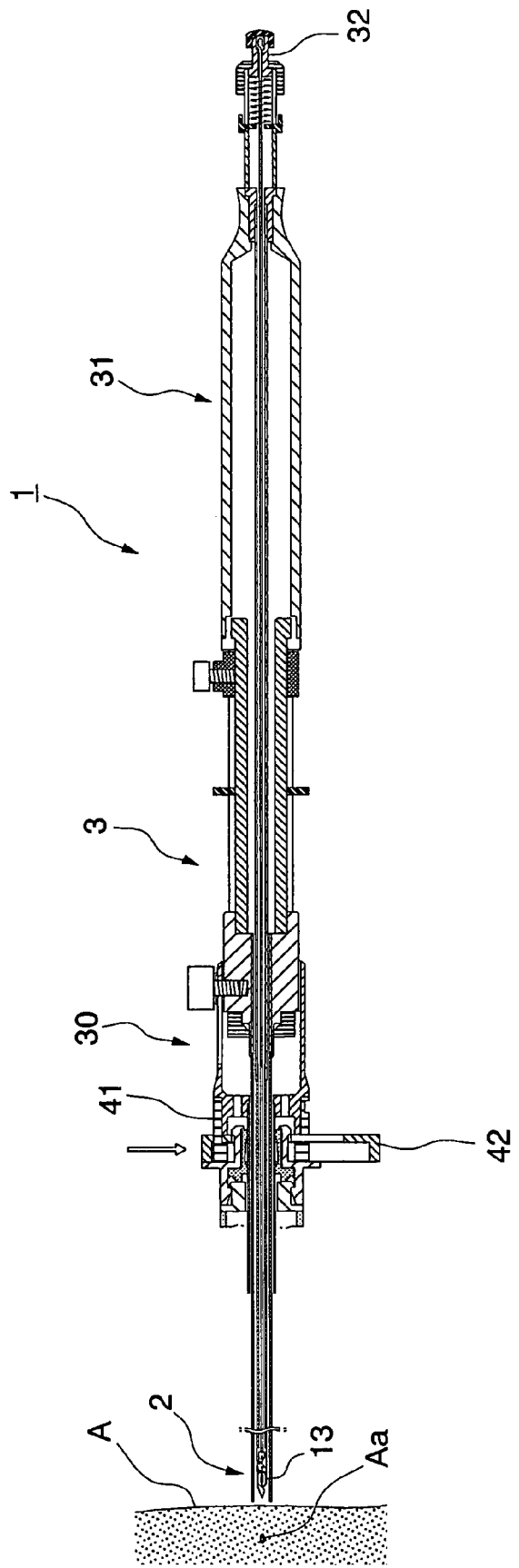
FIG. 10 is a cross-sectional view for explaining a step of the medical procedure according to the embodiment.

Specifically, the outer sheath 10 having the coil sheath 11, the forcep cups 13, and the like inserted and set therein, is inserted into the channel. As shown in FIG. 8, the adaptor forceps plug 44 is fitted on the channel insertion port 43. Furthermore, the coupling member 41 is moved to the channel insertion port 43 side to fit to the adaptor forceps plug 44 (refer to FIG. 9). In this condition, as shown in FIG. 10, the lock member 42 is moved in the direction orthogonal to the axis of the coupling member 41 to lock. As a result, the treatment tool for an endoscope 1 is fixed so as not to drop from the endoscope accidentally.

Next, the insertion portion of the endoscope having the treatment tool for an endoscope 1 set therein, is inserted from a natural orifice such as the mouth or the anus of the examinee into the body cavity, so that its distal end reaches the vicinity of a diagnosis site Aa of a parenchymatous organ A.

Figure 11:
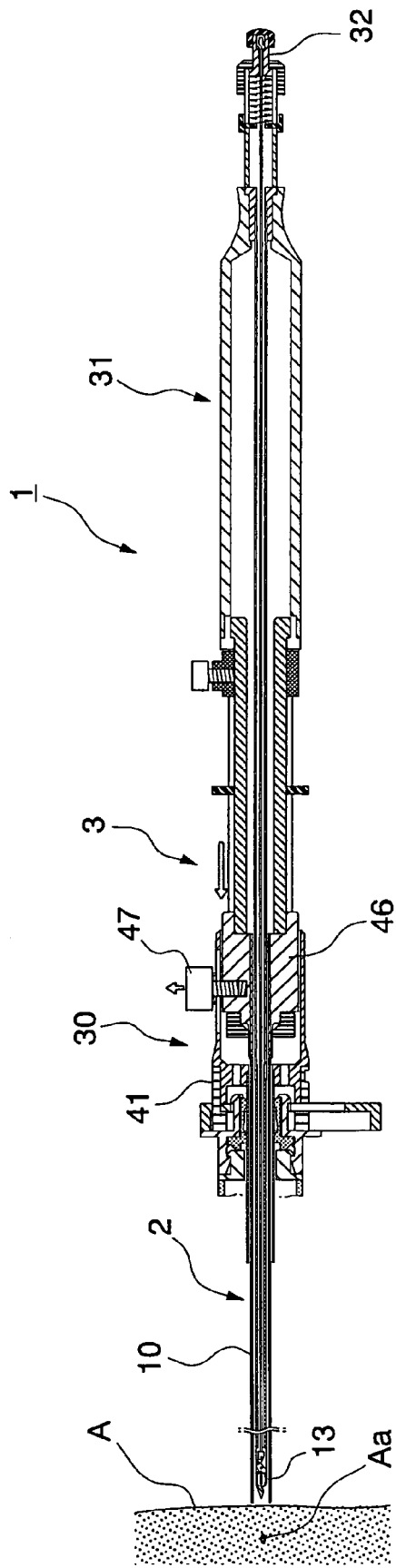
FIG. 11 is a cross-sectional view for explaining a step of the medical procedure according to the embodiment.

Next, as shown in FIG. 11, the screw 47 of the sheath fixed position adjustment mechanism 50 is loosened, and the pipe fixing member 46 is moved to the distal side of the coupling member 41, to adjust the position so that the distal end of the outer sheath 10 slightly projects from the exit of the channel opened in the distal end of the endoscope insertion portion. In this condition, the screw 47 is tightened. The position of the distal end of the outer sheath 10 at this time is a position which allows an appropriate observation respectively in an optical observation system and an ultrasonic observation system attached to the distal end of the endoscope insertion portion.

Figure 12:
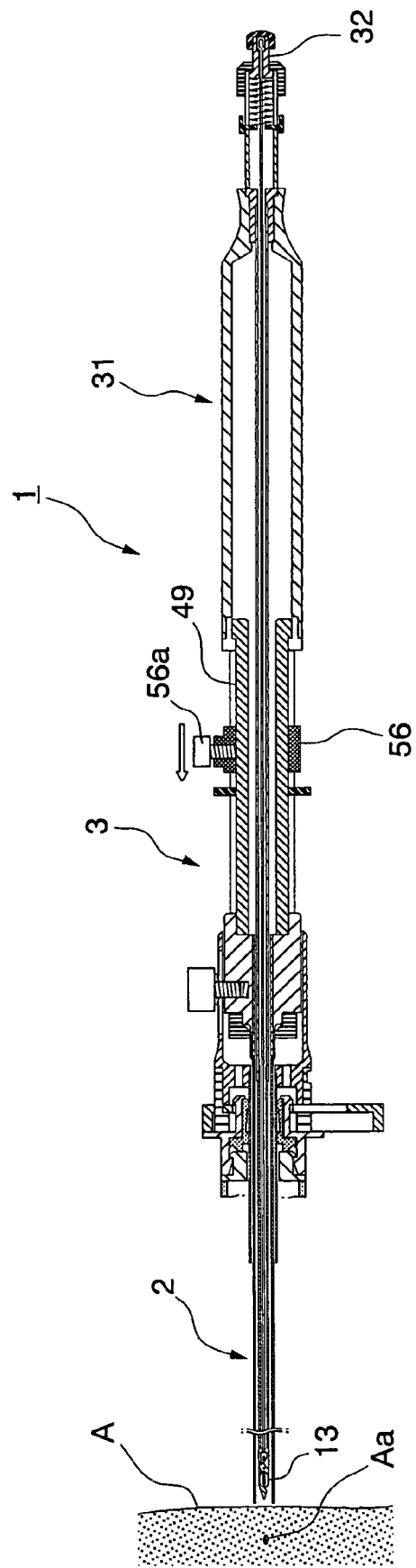
FIG. 12 is a cross-sectional view for explaining a step of the medical procedure according to the embodiment.

Next, as shown in FIG. 12, the screw 56a is loosened, and the stopper 56 is moved to the distal side along the axial direction of the slider receiver 49 so as to reach a position slightly before the C ring 57. This position of the stopper 56 serves as a guidance for moving the slider mainbody 52 to the distal side. As a result, as described later, the operator can operate to move the slider mainbody 52 with a sense of security.

Figure 13:
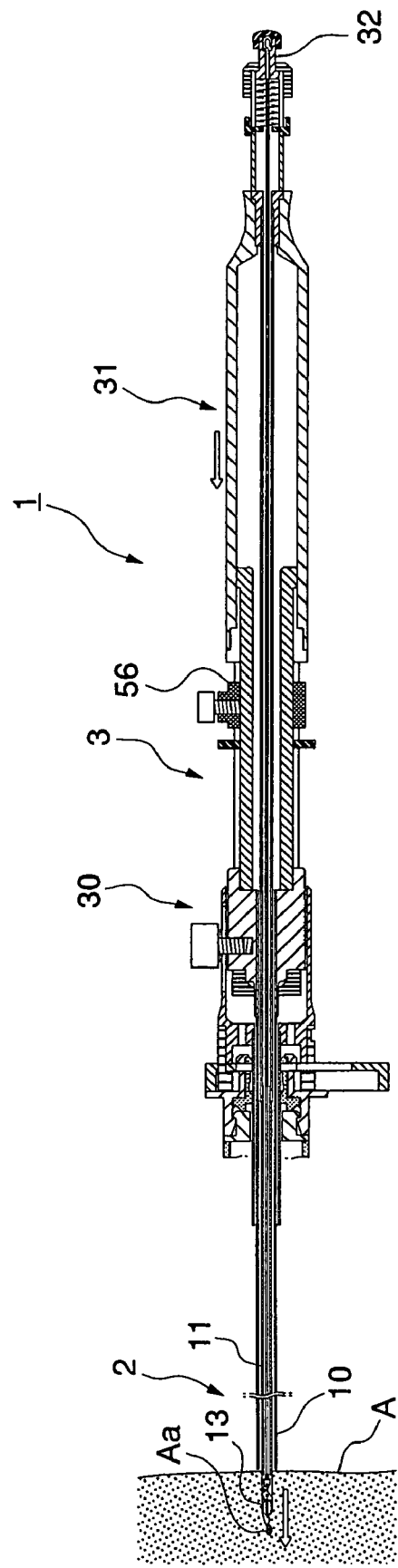
FIG. 13 is a cross-sectional view for explaining a step of the medical procedure according to the embodiment.

Next, as shown in FIG. 13, the operator grasps the slider mainbody 52 with his/her hand and moves it to a position where its distal end is abutted against the stopper 56.

Figure 14:
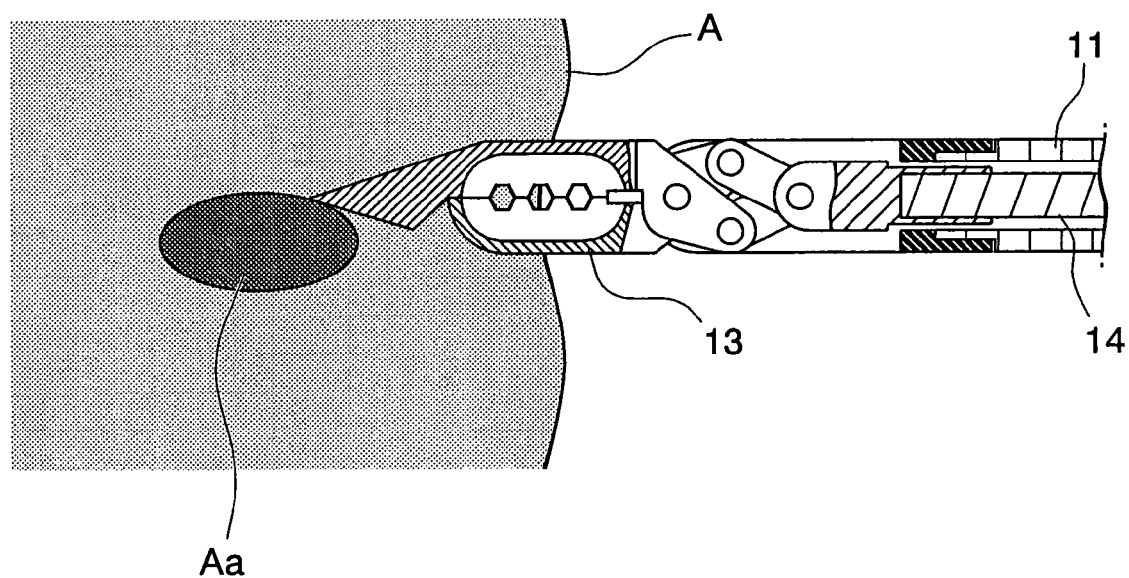
FIG. 14 is an enlarged cross-sectional view of a distal end of the treatment tool for an endoscope for explaining a step of the medical procedure according to the embodiment.

As a result, the coil sheath 11 and the forceps cups 13 attached to the distal end of the coil sheath 11 are moved to the distal side, and the forceps cups 13 project from the outer sheath 10. Then, the distal end of the forcep cups 13 pierces to the diagnosis site Aa of the parenchymatous organ A (refer to FIG. 14). At this time, since the forcep cups 13 have a sharp needle-shaped portion 12 formed on the distal end, the forcep cups 13 themselves can pierce to the diagnosis site Aa of the parenchymatous organ A, without using a treatment tool exclusively for piercing, nor a treatment tool for incision.

Next, as shown in FIG. 15 and FIG. 16, while pushing the button 32 attached to the proximal side of the slider mainbody 52 against the urging force of the coil spring 61 with the thumb, the slider mainbody 52 is further moved to the distal side up to the position where the stopper 56 is abutted against the C ring 57.

By pushing the button 32, the operation wire 14 is relatively moved to the distal side with respect to the coil sheath 11, and thereby the forcep cups 13 are opened. The slider mainbody 52 is further moved to the distal side, and thereby the forcep cups 13 are moved to the distal side via the coil sheath 11. That is, the forcep cups 13 are opened and moved to the distal side at the same time, to be faced to the diagnosis site Aa inside the parenchymatous organ A (refer to FIG. 17).

Such an operation simply involves grasping the slider mainbody 52 with one hand, pushing the button 32 with the thumb as it is, and pushing the grasped slider mainbody 52 into the distal side. Therefore, it is extremely easy even for only one operator to perform.

Next, as shown in FIG. 18, the pressing on the button 32 is released. As a result, the operation wire 14 is moved to the proximal side due to the urging force of the coil spring 61, and the forcep cups 13 are closed. That is, the biopsy tissue of the diagnosis site Aa is collected by the forcep cups 13. In this operation also it is sufficient to merely release the pressing operation of the button by means of the thumb, and hence it is also a very easy operation.

Figure 19:
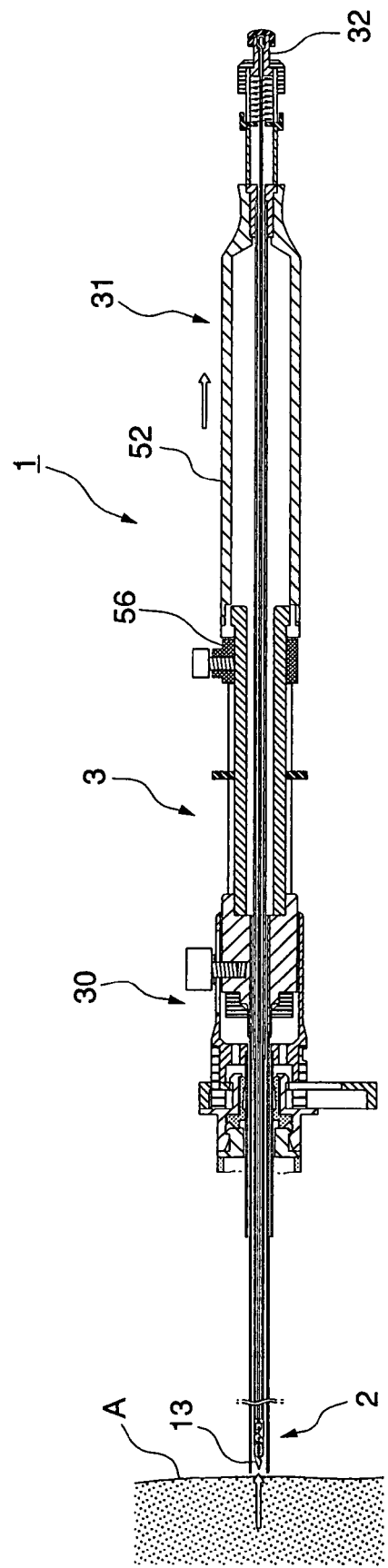
FIG. 19 is a cross-sectional view for explaining a step of the medical procedure according to the embodiment.

Next, as shown in FIG. 19, the slider mainbody 52 and the stopper 56 are moved to the proximal side to respectively return to the original position.

Figure 20:
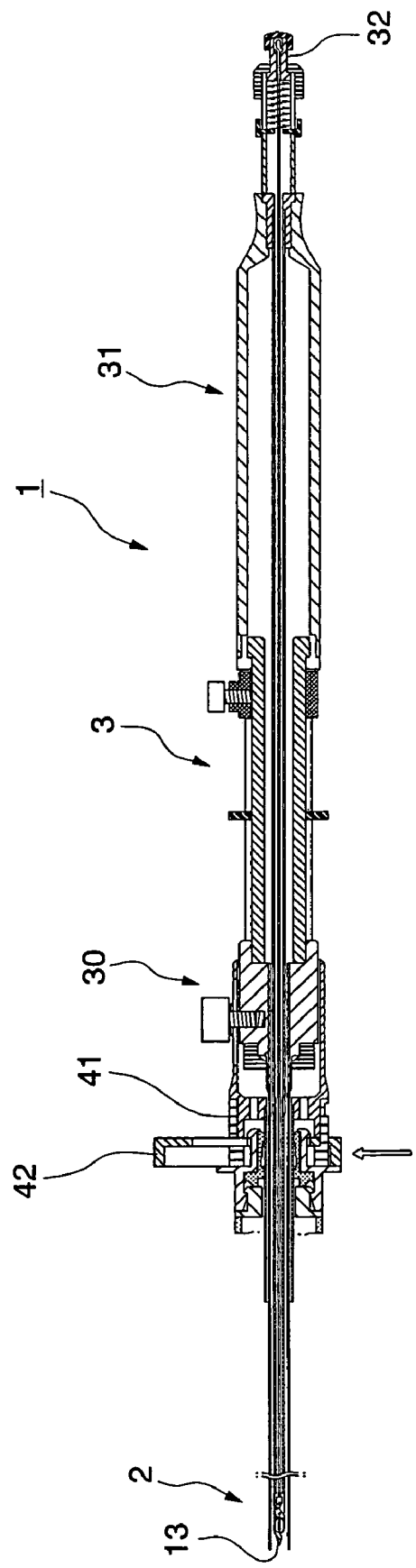
FIG. 20 is a cross-sectional view for explaining a step of the medical procedure according to the embodiment.

Next, as shown in FIG. 20, the lock member 42 is moved in the direction orthogonal to the axis of the coupling member 41 to return to the original position.

Figure 21:
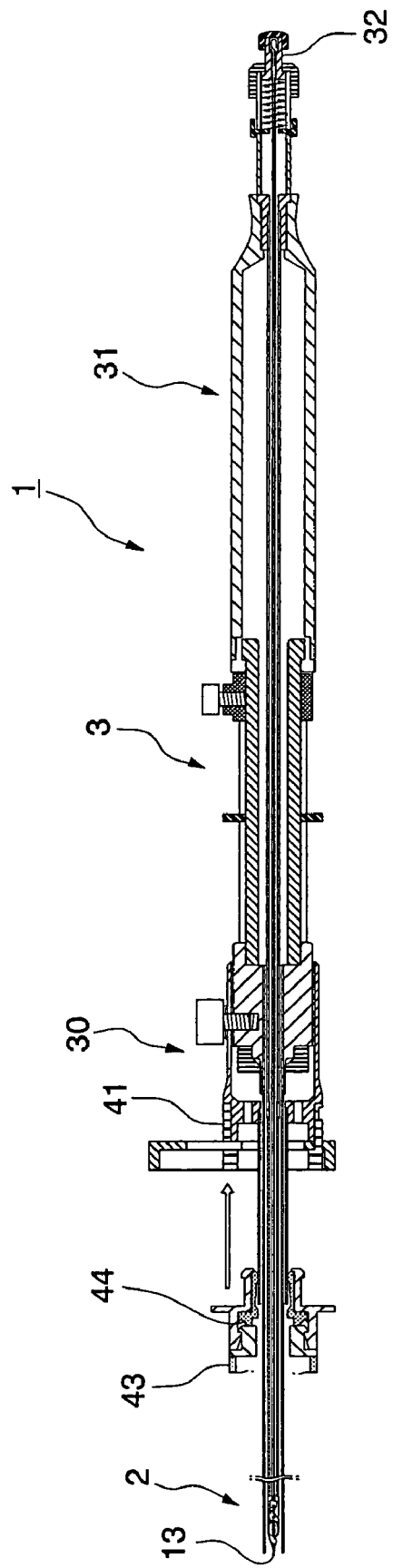
FIG. 21 is a cross-sectional view for explaining a step of the medical procedure according to the embodiment.

Lastly, as shown in FIG. 21, the engagement of the coupling member 41 and the adaptor forceps plug 44 is released, after which the treatment tool for an endoscope 1 is withdrawn from the channel of the endoscope.

By the above operation, the biopsy tissue of the diagnosis site Aa can be collected from the inside of the parenchymatous organ A of the examinee.

Here is a description of modified examples of the embodiment.

First Modified Example

Figure 22:
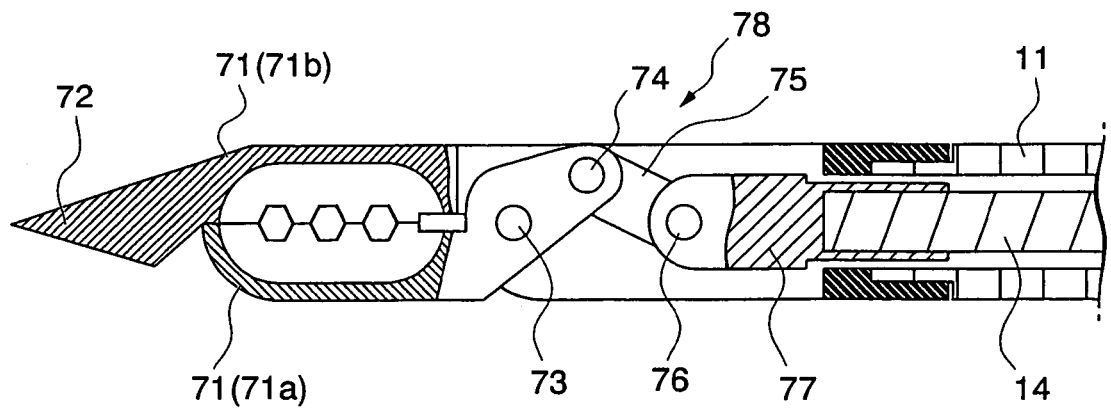
FIG. 22 is an enlarged cross-sectional view for explaining a first modified example of the forcep cups.
Figure 23:
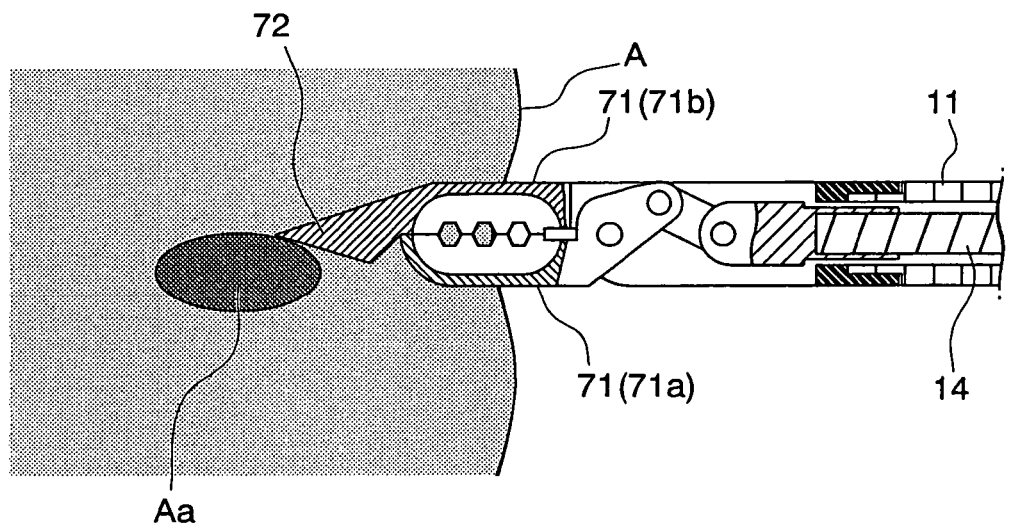
FIG. 23 is an enlarged cross-sectional view for explaining the medical procedure using the first modified example of the forcep cups.
Figure 24:
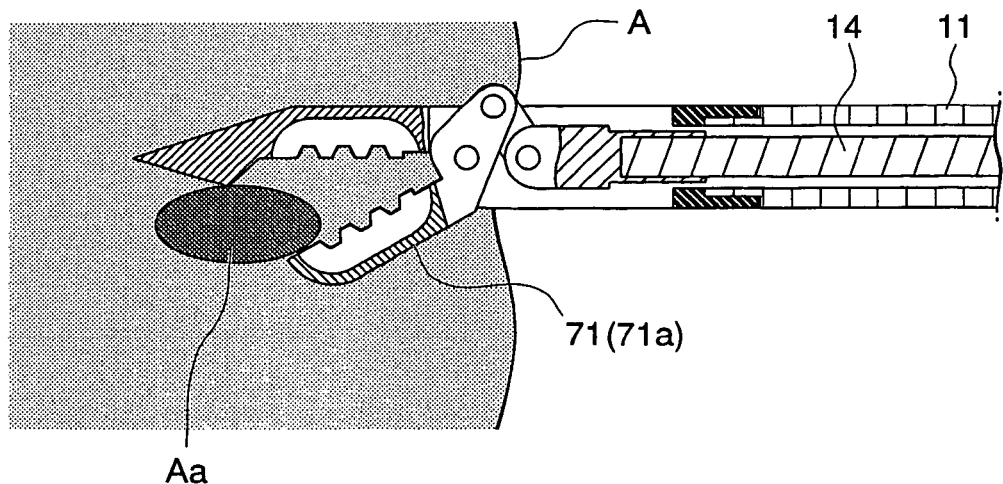
FIG. 24 is an enlarged cross-sectional view for explaining the medical procedure using the first modified example of the forcep cups.

FIG. 22 to FIG. 24 show a first modified example of the forcep cups.

In the abovementioned forcep cups 13, when the operation wire 14 is moved to the distal side to open, both forcep cups 13 respectively rotate about the pin 16. However, in this modified example, only one forcep cup 71a of a pair of forcep cups 71 (71a and 71b) rotates, and the other forcep cup 71b does not rotate.

That is, the other forcep cup 71b is attached to the distal end of the coil sheath 11 in a manner where it is integrally fixed to the connection part to be connected with the coil sheath 11. The intermediate portion of the one forcep cup 71a is rotatably attached to the intermediate portion of the other forcep cup 71b, via a pin 73. The proximal end of the one forcep cup 71a is linked to the distal end of a link member 75 via a pin 74. The proximal end of the link member 75 is linked to a coupling rod 77 via a pin 76. The coupling rod 77 is linked to the distal end of the operation wire 14.

That is, the one forcep cup 71a, the link member 75, and the coupling rod 77 constitute the link mechanism 78. By this link mechanism 78, only one forcep cup 71a rotates to open when the operation wire 14 is moved to the distal side with respect to the coil sheath 11 as shown in FIG. 24, and only one forcep cup 71a rotates to close when the operation wire 14 is moved to the proximal side with respect to the coil sheath 11 as shown in FIG. 23.

Moreover, only the distal end of the other forcep cup 71b is formed with a needle-shaped portion 72 which is sharp in a conical shape. The distal end of the one forcep cup 71a is not formed with a needle-shaped portion.

Next a method of collecting the biopsy tissue from the inside of the parenchymatous organ A using these forcep cups 71 is described for only the points different from the abovementioned method.

Firstly, as shown in FIG. 23, the coil sheath 11 is moved to the distal side, and the vicinity of the diagnosis site Aa of the parenchymatous organ A is pierced with the forceps cups 71 using the needle-shaped portion 72 formed on the distal end of the forceps cups 71. At this time, the needle-shaped portion 72 is formed on the other forcep cup 71b serving as the non-movable forcep cup that is directly fixed to the coil sheath 11. Therefore when the coil sheath 11 is pressed to move, the pressing force is directly transferred to the needle-shaped portion 72, enabling smooth piercing by the forceps cups 71.

Next, while the coil sheath 11 is further moved to the distal side, a button (not shown) is pressed at the same time, so as to move the operation wire 14 forward. As a result, as shown in FIG. 24, while the one forcep cup 71a is being opened, the whole forcep cups 71 are moved to the distal side at the same time, so as to face the diagnosis site Aa inside the parenchymatous organ A.

Here, in the forcep cups 71, both cups are not opened, but only the one forcep cup 71a not having the needle-shaped portion 72 on the distal end is opened. As a result, at the time of the opening operation, less resisting force from the parenchymatous organ is received, so that a smooth opening operation is performed.

Incidentally, when the forcep cups each formed with needle-shaped portions on the distal ends are opened, the needle-shaped portions rotate respectively while piercing the parenchymatous organ, and as a result a greater resisting force is received from the parenchymatous organ.

Second Modified Example

Figure 25:
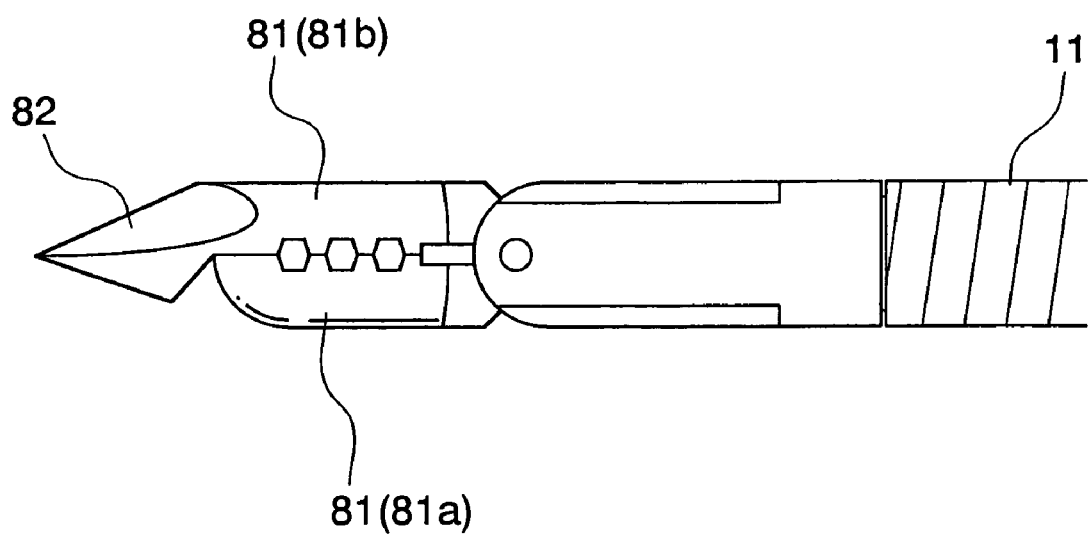
FIG. 25 is an enlarged side view showing a second modified example of the forcep cups.
Figure 26:
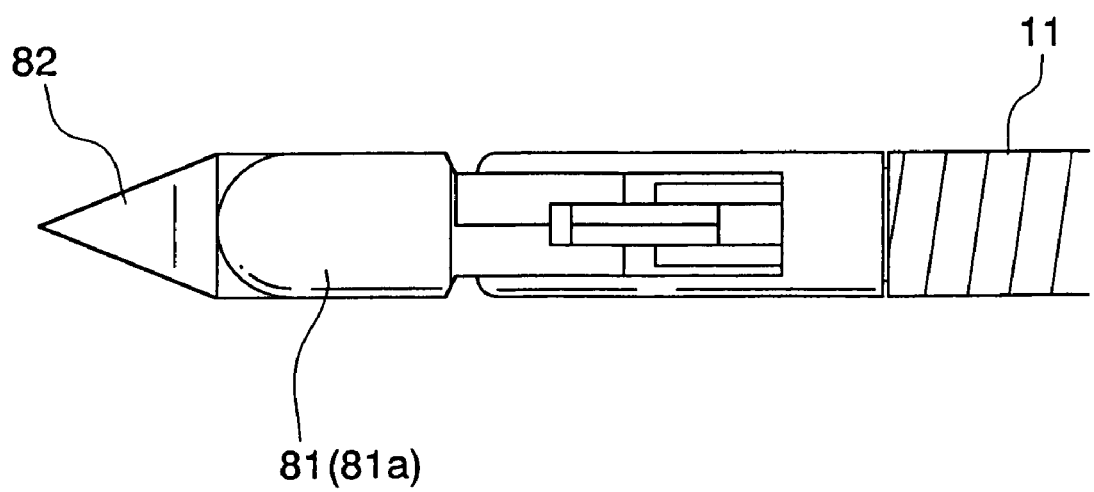
FIG. 26 is an enlarged bottom view showing the second modified example of the forcep cups.

FIG. 25 and FIG. 26 show a second modified example of the forcep cups.

In this modified example, a needle-shaped portion 82 formed on the distal end of forcep cups 81 (81a and 81b) has the distal end formed in a triangular pyramid shape (trocar point). Moreover, the needle-shaped portion 82 is not formed on both forcep cups 81a and 81b, but is formed only on one forcep cup 81b. In this modified example, both forcep cups 81a and 81b rotate.

Third Modified Example

Figure 27:
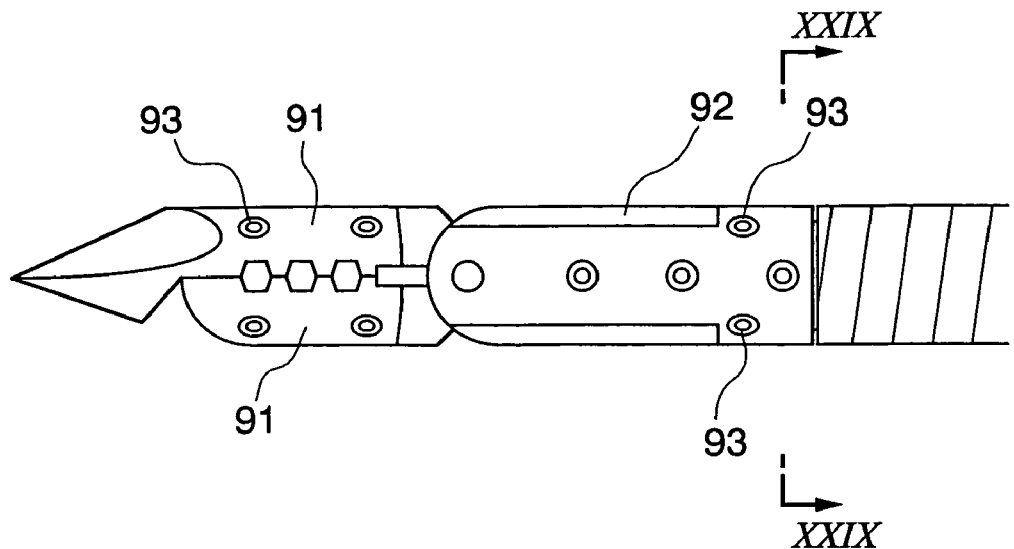
FIG. 27 is an enlarged side view showing a third modified example of the forcep cups.
Figure 28:
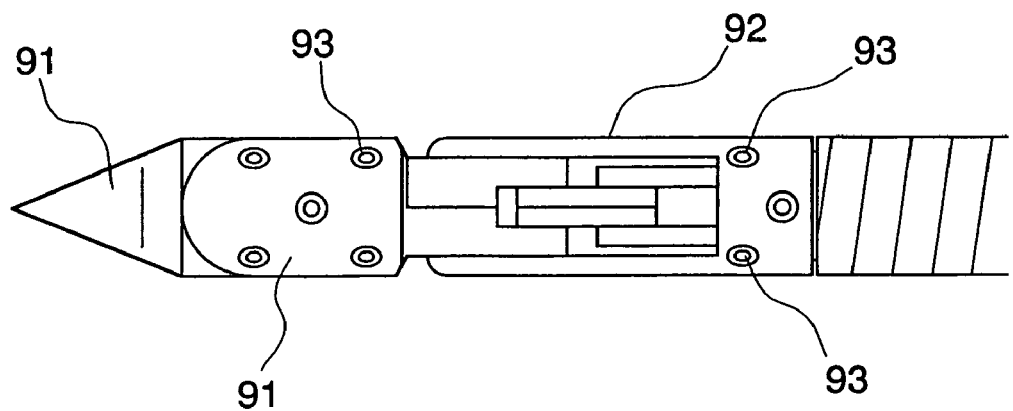
FIG. 28 is an enlarged bottom view showing the third modified example of the forcep cups.
Figure 29:
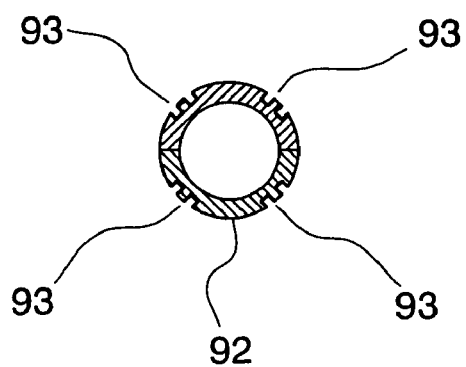
FIG. 29 is an enlarged transverse cross-sectional view taken along the line XXIX-XXIX of FIG. 27 showing the third modified example of the forcep cups.

FIG. 27 to FIG. 29 show a third modified example of the forcep cups.

The difference of this modified example from the above-mentioned forcep cups shown in FIG. 25 and FIG. 26, is the point that the surfaces of the forcep cups 91 and a base plate 92 are respectively provided with a plurality of dimple portions 93.

In this manner, by providing the surfaces of the forcep cups 91 and the base plate 92 with the dimple portions 93, reflected waves from the dimple portions 93 are received, enabling the location of the forcep cups and the base plate to be accurately ascertained, and facilitating the collection operation of the diagnosis site inside the parenchymatous organ under an ultrasonic image.

Fourth Modified Example

Figure 30:
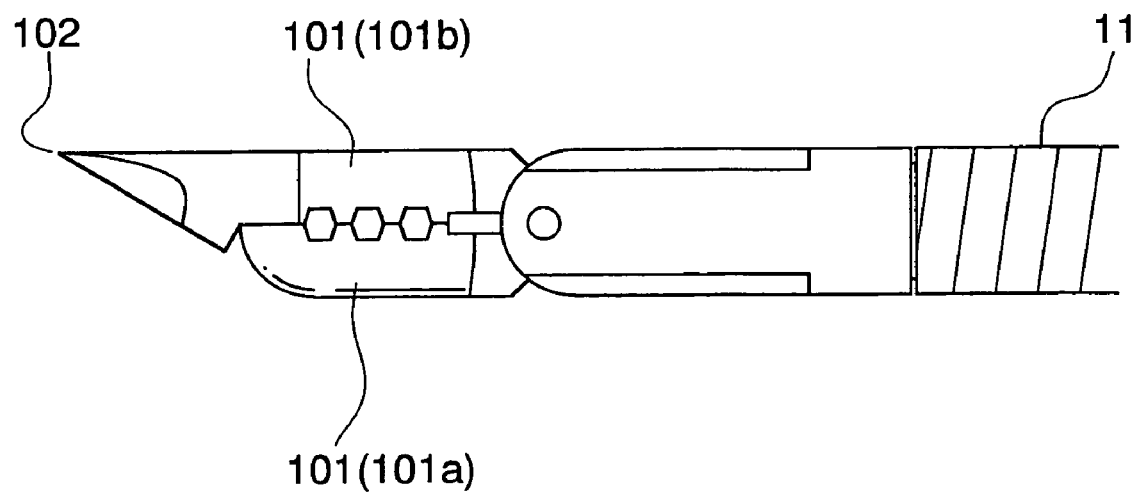
FIG. 30 is an enlarged side view showing a fourth modified example of the forcep cups.
Figure 31:
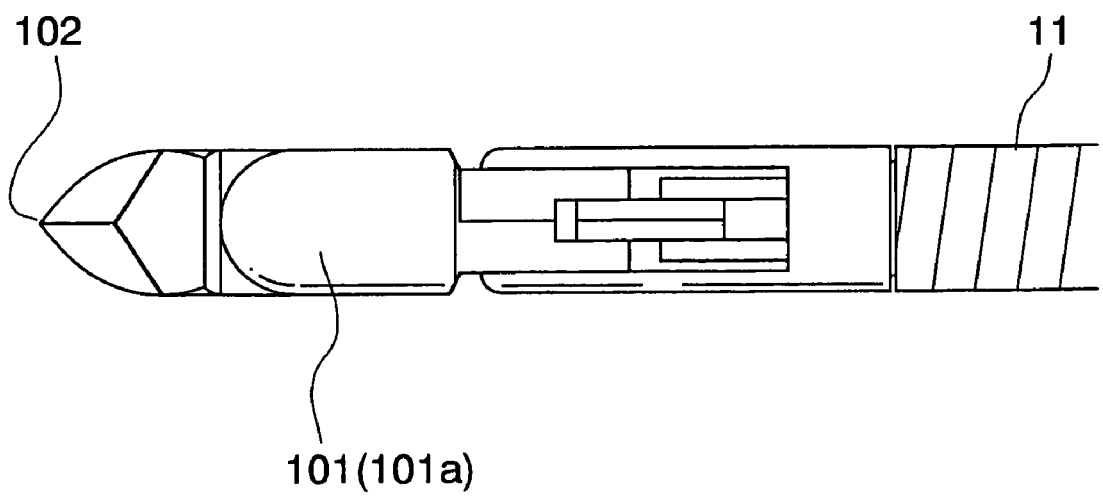
FIG. 31 is an enlarged bottom view showing the fourth modified example of the forcep cups.

FIG. 30 and FIG. 31 show a modified example of the forcep cups.

In this modified example, a needle-shaped portion 102 formed on the distal end of forcep cups 101 (101a and 101b) has a shape where the distal end is cut slantwise from bottom to top in FIG. 30, and both sides of this cut portion are further cut slantwise (lancet point). Moreover, also in this modified example, the needle-shaped portion 102 is not formed on the both forcep cups 101a and 101b, but is formed only on one forcep cup 101b. Also in this modified example, both forcep cups 101a and 101b rotate.

The technical scope of the present invention is not limited to the above embodiments, and various modifications can be made without departing from the scope of the present invention.

For example, in the above embodiments, the description is for examples where there are two forcep cups 13, 71 (71a and 71b), 81 (81a and 81b), 91, and 101 (101a and 101b). However it is not limited to this and there may be three forcep cups or more.

Moreover, in the above embodiments, the configuration is such that the button 32 which opens/closes the forcep cups is automatically returned by the coil spring 61. However it is not limited to this and the button may be automatically returned by another elastic member such as a rubber member. Furthermore, the configuration may be such that the operator manually returns the button without using the elastic member.

Furthermore, in the above embodiments, only one forcep cup is formed with the needle-shaped portion. However it is not limited to this and a plurality of forcep cups may be respectively provided with needle-shaped portions.

Moreover, in the above embodiments, the insertion port 43 of the channel of the endoscope comprises the coupling member 41 and the lock member 42 for fixing the treatment tool for an endoscope. However these members 41 and 42 are not always necessary, and the present invention may be realized without them. Moreover, similarly, the present invention may be realized without the screw 47 for adjusting the position of the pipe fixing member 46 with respect to the coupling member 41.

What is claimed is:

1. A treatment tool for an endoscope comprising:
    an outer sheath to be inserted into a channel of an endoscope;
    a forcep sheath which is movably arranged in the outer sheath along an axial direction;
    a plurality of forcep cups which are attached to a distal end of the forcep sheath, at least one of which is formed with a sharp needle-shaped portion on a distal end, and which cooperate with each other to be openable/closable as a whole;
    an operation wire which is movably arranged in the forcep sheath along an axial direction, and is connected to the forcep cups, and which opens/closes the forcep cups when moved in its axial direction;
    a first operation portion which is movably attached along an axial direction of a proximal end of the outer sheath, and is connected to a proximal end of the forcep sheath; and
    a second operation portion which is movably attached to the first operation portion along an axial direction of the proximal end of the forcep sheath, is connected to a proximal end of the operation wire, and is configured to receive a pressing operation by an operator, wherein
    the second operation portion is provided with an elastic member which returns the second operation portion to an original position when the pressing operation by the operator is released,
    the treatment tool further comprises an elastic member stopper, wherein the elastic member is sandwiched between the second operation portion and the elastic member stopper, and
    the elastic member stopper is positioned by a positioning mechanism in a plurality of axially spaced positions including a free position where the elastic member is not contacted by the second operation portion.

2. The treatment tool for an endoscope according to claim 1, further comprising an endoscope coupling tool which is connected to the proximal end of the outer sheath and is fixed to an insertion port of the channel of the endoscope.

3. The treatment tool for an endoscope according to claim 2, wherein the first operation portion includes a pipe-shaped handle that is to be grasped by an operator's hand.

4. The treatment tool for an endoscope according to claim 3, wherein the second operation portion includes a button which is provided on a proximal end of the pipe-shaped handle constituting the first operation portion, and is pressed by a finger of the operator's hand grasping the pipe-shaped handle.

5. The treatment tool for an endoscope according to claim 2, further comprising a first operation portion stopper which determines a movement limit position when the first operation portion is moved to the endoscope coupling tool side.

6. The treatment tool for an endoscope according to claim 2, wherein the endoscope coupling tool includes a sheath fixed position adjustment mechanism which, when fixed to the insertion port of the channel of the endoscope, moves and adjusts a fixed position of the proximal end of the outer sheath along the axial direction of the proximal end of the outer sheath.

7. The treatment tool for an endoscope according to claim 2, wherein the endoscope coupling tool comprises a lock member configured to fix the treatment tool to the endoscope by a sliding operation of the lock member.

8. The treatment tool for an endoscope according to claim 1, wherein only one forcep cup among a plurality of the forcep cups is formed with the sharp needle-shaped portion.

9. The treatment tool for an endoscope according to claim 8, wherein only a forcep cup not formed with the sharp needle-shaped portion among a plurality of the forcep cups is openable/closable.

10. The treatment tool for an endoscope according to claim 1, wherein all forcep cups among a plurality of the forcep cups are formed with the sharp needle-shaped portions.

* * * * *